(12) United States Patent
Suzuki et al.

(10) Patent No.: US 6,706,865 B2
(45) Date of Patent: Mar. 16, 2004

(54) PROCESS FOR PREPARING FLAVONOIDS

(75) Inventors: Keisuke Suzuki, Yokohama (JP); Ken Ohmori, Kawasaki (JP)

(73) Assignee: Daiichi Suntory Pharma Co., Ltd., Tokyo (JP)

( * ) Notice: Subject to any disclaimer, the term of this patent is extended or adjusted under 35 U.S.C. 154(b) by 0 days.

(21) Appl. No.: 10/220,202

(22) PCT Filed: Mar. 5, 2001

(86) PCT No.: PCT/JP01/01674

§ 371 (c)(1),
(2), (4) Date: Nov. 21, 2002

(87) PCT Pub. No.: WO01/64701

PCT Pub. Date: Jul. 9, 2001

(65) Prior Publication Data

US 2003/0162728 A1 Aug. 28, 2003

(30) Foreign Application Priority Data

Mar. 3, 2000 (JP) .......................... 2000-059278

(51) Int. Cl.⁷ .................................. C07H 1/00
(52) U.S. Cl. ........................... 536/8; 536/18.5
(58) Field of Search ..................... 536/8, 18.5

(56) References Cited

FOREIGN PATENT DOCUMENTS

JP    6-247851    6/1994

OTHER PUBLICATIONS

Ken Ohmori, et al., "First synthesis of astiblin biologically active glycosyl flavonoid isolated from Chinese folk medicine" Tetrahedron Letters, vol. 41, (Jul. 15, 2000) pp. 5537–5541.

*Primary Examiner*—Elli Peselev
(74) *Attorney, Agent, or Firm*—Crowell & Moring LLP

(57) ABSTRACT

A simple and easy process for preparing pharmacologically useful flavonoid compound having reductase inhibitory effect, active oxygen extinguishing effect, carcinogenesis promotion inhibitory effect, anti-inflammatory effect, and so on. Particularly, a process for preparing the compound of the formula (I):

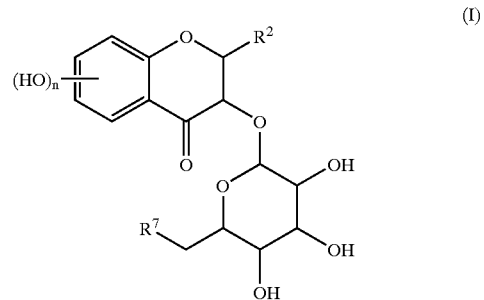

wherein, $R^2$ is a substituted or un-substituted phenyl group; $R^7$ is a hydrogen atom or a hydroxyl group; and n is an integer of 1 to 4;

by bonding a sugar derivative to catechins as the starting compound selectively via O-glycoside bond and then oxidizing the 4-position of flavanoid skeleton of the obtained compound.

9 Claims, No Drawings

PROCESS FOR PREPARING FLAVONOIDS

This application is a 371 of PCT/JP01/01674 filed Mar. 5, 2001.

TECHNICAL FIELD

The present invention relates to a process for preparing flavonoid compound useful for treating many kinds of diseases due to their aldose reductase inhibitory effect, active oxygen extinguishing effect, carcinogenesis promotion inhibitory effect, anti-inflammatory effect, and so on. More particularly, the present invention relates to a process for preparing astilbin, neoastilbin, isoastilbin, neoisoastilbin, cuersetin, smitilbin, engeletin, and analogous thereof.

BACKGROUND ART

Astilbin represented by the following formula (I-c):

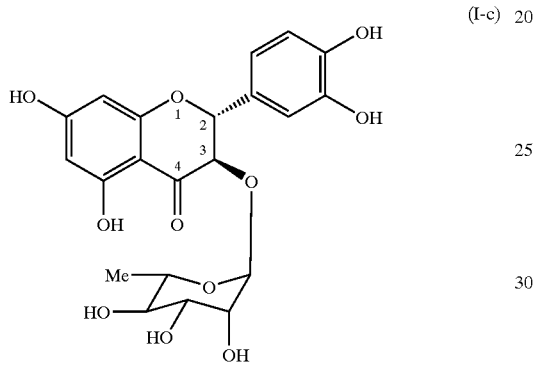

is one of dihydroflavonol glycoside isolated from root of *Astilbe thunbergii* Miq., which is herbaceous perennial of saxifragaceous, as well as from the plant matter of Asmilaxylabra, Engelhardtia, Lyoniaovalifolia, Engelhardtiachrysolepis, *Chloranthus glarber*, Astilbe, microphylla, and so on. There has been reported that astilbin exhibits some important bioactivities such as aldose reductase inhibitory effect, active oxygen extinguishing effect, carcinogenesis promotion inhibitory effect, anti-inflammatory effect, and so on (Japanese Patent Publication Nos. 97/30984, 94/65074, 94/247851, and 94/256194), and therefore, astilbin is to be a very useful compound as anti-allergic drug or anticancer drug.

Astilbin of the formula (I-c) is a specific compound having two asymmetric carbon atoms at 2- and 3-positions of flavan skeleton, and rhamnose group is substituted at 3-position via O-glycosyl bound. A stereoisomer of astilbin, that is, neoastilbin, isoastilbin and neoisoastilbin, have same biological effects as those of astilbin, and further smitilbin or engeletin, analogous compound of astilbin, has improving effect for immune hepatic toxicity (*Planta Med.*, 1999 February, 65(1): 56–59).

It has been known that astilbin or analogues thereof, including stereoisomeric compound, was obtained from plant matter (e.g., *Astilbe thunbergii* Miq) by isolating and purification procedures. Further, the method for isomerising of astilbin and stereoisomer thereof using basic aqueous solution has only been reported (Yakugaku Zasshi, 1959, 80: 1202), and therefore, a chemical total synthesis of astilbin is not established up to now.

Hence the content of the objective compound in the plant matter is varied depending on the picking season, picking place and so on, and is very low, the isolating procedure from the plant matter is not available for industrial methods of producing said compound. Further, using the compound isolated from the plant matter as a medicine has some troubles due to the difficulties of separating from the analogous compounds and purifying the compound.

Accordingly, the object of the present invention is to provide a process for preparing a flavonoid compound having aldose reductase inhibitory effect, active oxygen extinguishing effect, carcinogenesis promotion inhibitory effect, anti-inflammatory effect, and so on. More particularly, the object of the present invention is to provide the industrial process for preparing astilbin and analogous thereof from the easily obtainable starting compound with short process and convenient means in high yield and high purity of the compound.

DISCLOSURE OF INVENTION

In order to solve the problems, therefore, the present inventors have found out that starting from readily available catechins, and reacting catechins with saccharides to obtain O-glycoside compounds then, oxidizing the C(4) position of flavonoid skeleton of obtained compounds to produce astilbin and analogous thereof in high yield by selectively process.

Accordingly, one aspect of the present invention is to provide a process for preparing a compound represented by the following formula (I):

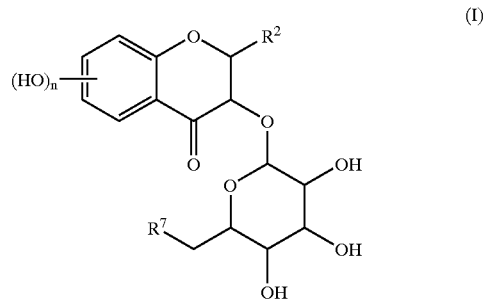

wherein, $R^2$ is a substituted or unsubstituted phenyl group; $R^7$ is a hydrogen atom or a hydroxyl group; and n is an integer of 1 to 4, which process is characterized in that reacting a compound of the following formula (II):

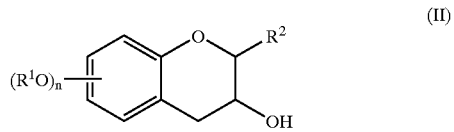

wherein, $R^1$ is a hydroxyl protecting group; $R^2$ and n have the same meanings mentioned above, with a sugar compound of the following formula (III):

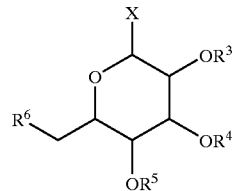

(III)

wherein, $R^3$, $R^4$ and $R^5$ are independently each other, a hydrogen atom or a hydroxyl protecting group; $R^6$ is a hydrogen atom, a hydroxyl group or a protected hydroxyl group; and X is a halogen atom or an acyloxy group, to produce a compound of following formula (IV):

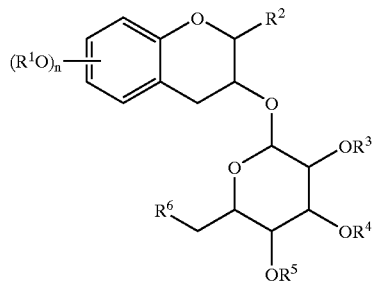

(IV)

wherein, $R^1$, $R^2$, $R^3$, $R^4$, $R^5$, $R^6$ and n have the same meanings mentioned above, then, conducting (a) or (b);

(a) oxidizing of 4-position of the flavonoid skeleton of the compound of the formula (IV) obtained above to produce a compound of the following formula (V):

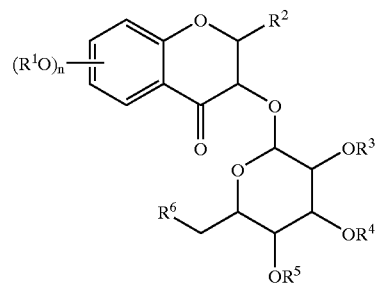

(V)

wherein, $R^1$, $R^2$, $R^3$, $R^4$, $R^5$, $R^6$ and n have the same meanings mentioned above, or (b) oxidizing of 4-position of the flavonoid skeleton of the compound of the formula (IV) to produce a compound of the following formula (VI):

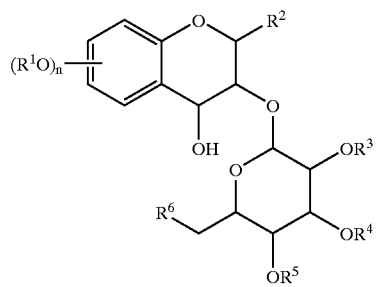

(VI)

wherein, $R^1$, $R^2$, $R^3$, $R^4$, $R^5$, $R^6$ and n have the same meanings mentioned above, subsequently, further oxidizing of 4-position of the flavonoid skeleton of the compound of the formula (VI) obtained above to produce a compound of the following formula (V):

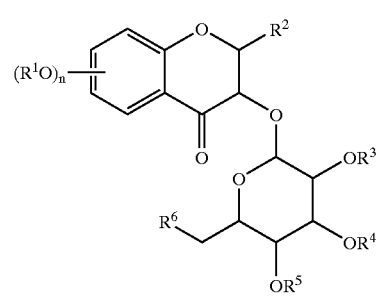

(V)

wherein, $R^1$, $R^2$, $R^3$, $R^4$, $R^5$, $R^6$ and n have the same meanings mentioned above, and finally, removing the hydroxyl protecting group of the compound (V), obtained by the above methods (a) or (b), to produce the compound of the formula (I).

Specific aspect of the present invention, it is provided a process for preparing a compound represented by the following formula (I-a):

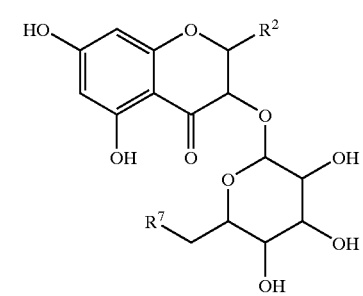

(I-a)

wherein, $R^2$ is a substituted or un-substituted phenyl group; $R^7$ is a hydrogen atom or a hydroxyl group.

More specific aspect of the present invention is to provide a process for preparing a compound represented by the following formula (I-b):

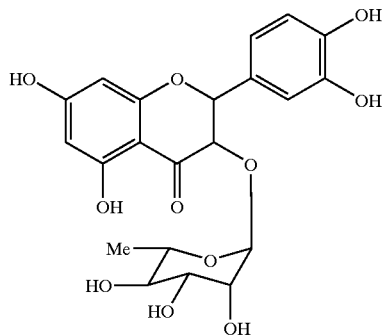

(I-b)

in which, the positions of hydroxyl groups at the flavonoid skeleton, and sugar derivative at 3-position are specified as mentioned above formula.

Still more specific aspect of the present invention is to provide a process for preparing a compound represented by the following formula (I-c):

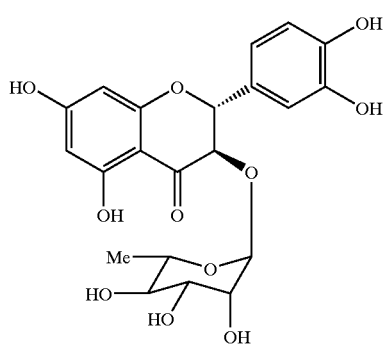

(I-c)

that is, astilbin itself.

For the synthetic method of the compound of the formula (I) or the compound of the formula (V), the direct reaction of flavonoid compound having hydroxyl group at the 3-position and oxo group at the 4-position with the corresponding sugar derivative is thought as one method. However, the objective compound can't obtain by this method due to the interaction of hydroxyl group at the 3-position and oxo group at the 4-position of flavonoid skeleton.

According to the process of the present invention, the compound of the formula (I) or the compound of the formula (V) can be prepared from readily available compound and by industrial short process with high yield, and therefore, the present invention is superior one.

BEST MODE FOR CARRYING OUT THE INVENTION

In the present specification, the substitute for the substituted phenyl group represented by "$R^2$" in the compound of formula (II) may be hydroxyl group; hydroxyl group protected by the protecting group of $R^3$, $R^4$, $R^5$, or $R^6$, described later; preferably straight or blanched alkyl group having 1 to 6 carbon atoms such as methyl, ethyl, propyl, isopropyl, butyl, isobutyl, tert-butyl, pentyl, hexyl, and the like; preferably straight or blanched alkoxy group having 1 to 6 carbon atoms such as methoxy, ethoxy, propoxy, isopropoxy, butoxy, tert-butoxy, and the like; amino group; amino group protected by the protecting group of $R^3$, $R^4$, $R^5$, or $R^6$, described later; amide group; substituted amide group; lower acyl group such as acetyl, propionyl, tert-butyroyl, benzoyl and the like. In addition, number of the substitute and position of the substitute are not limited respectively.

In the formula (III), halogen atom represented by "X" is chlorine, bromine, iodine and fluorine; acyloxy group may be lower acyloxy group such as acetyloxy, propionyloxy, tert-butyroyloxy and the like, and aromatic acyloxy group such as benzoyloxy, toluyloxy and the like.

The present invention of process for preparing astilbin and analogous thereof is described in more detail by explaining the each step in the following.

The following are chemical reaction scheme of process for preparing astilbin and analogous thereof of the present invention.

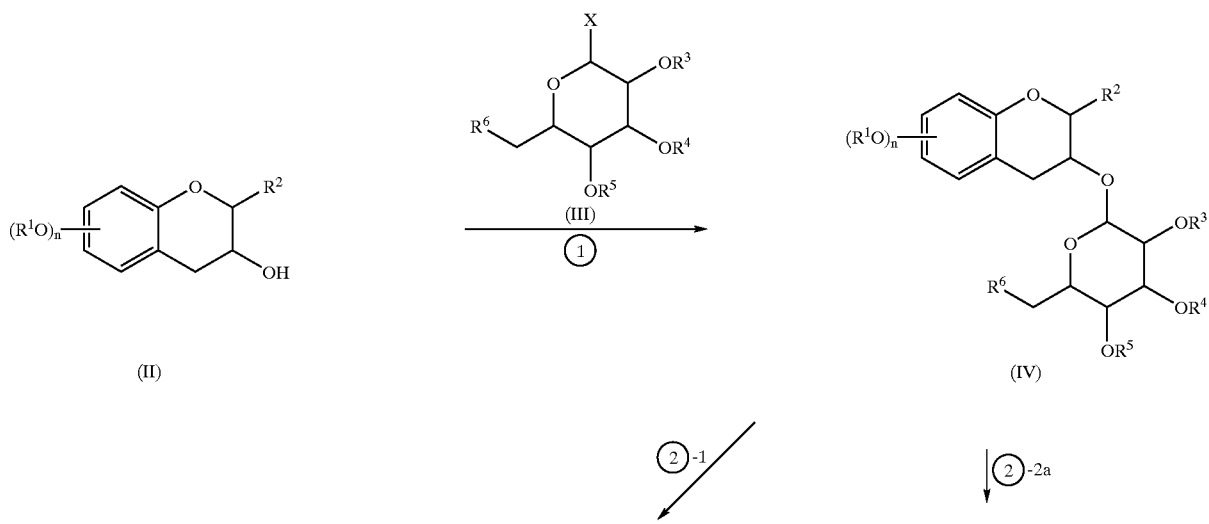

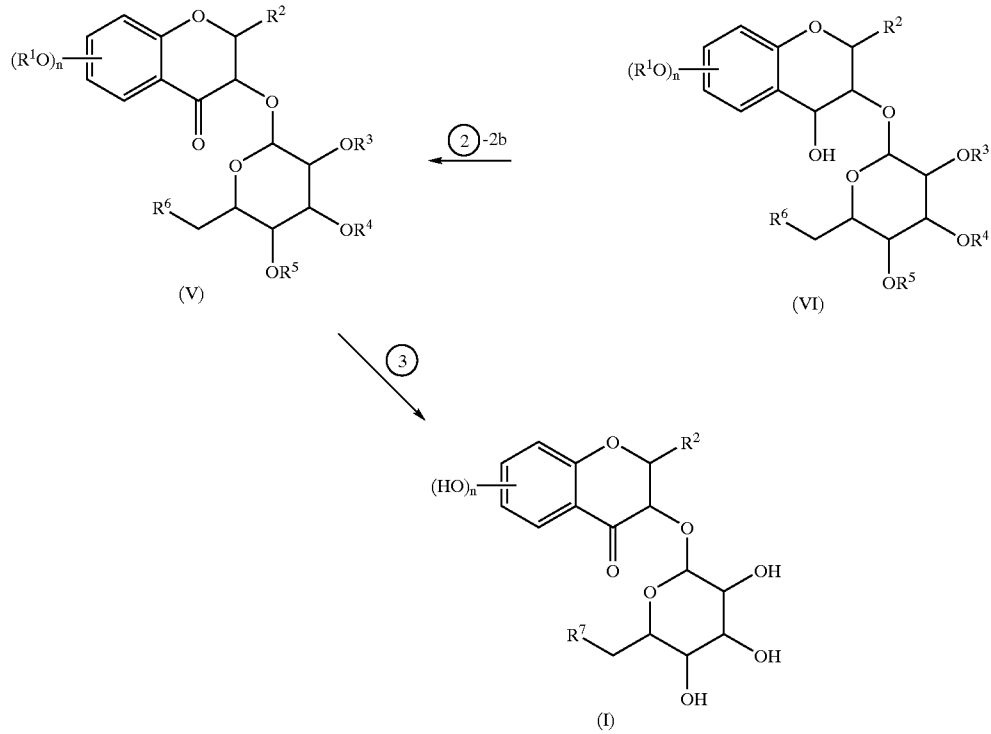

Wherein, $R^1$, $R^2$, $R^3$, $R^4$, $R^5$, $R^6$, $R^7$, X and n have the same meanings mentioned above, and number in ○ denotes process number.

The process of the present invention is comprises the Process 1 which is the process for preparing the compound of the formula (IV) by reacting catechins having protected hydroxyl group represented by the formula (II) with sugar derivatives of the formula (III); the Process 2 which is the process for preparing the compound of the formula (V) by oxidizing the compound (IV) obtained in the process 1; and the Process 3 which is the process for preparing the objective compound of the present invention represented by the formula (I) by removing the hydroxyl protecting group of the compound (V) obtained in the Process 2.

In the Process 2, which is the process for preparing the compound of the formula (V) by oxidation of the 4-position of flavonoid skeleton of the compound (IV), the reaction may be carried out by the following two methods (a) or (b).

(a) Method for obtaining the compound (V) by direct oxidation of the compound (IV) (Process ②-1), or (b) Method for obtaining the compound (V) by converting the compound (IV) to the intermediate compound of the formula (VI) by introducing hydroxyl group at 4-position of flavonoid skeleton of the compound (IV) (Process ②-2a), then oxidation of the hydroxyl group at the 4-position of the compound (VI) (Process ②-2b).

Each process is described in more detail in the following.

The Process 1 is the process for preparing the compound of the formula (IV) by reacting catechins having protected hydroxyl group of the formula (II) with sugar derivatives of the formula (III).

In catechins of the formula (II), substitute represented by "$R^2$" is substituted phenyl group. In case of the substitute of phenyl group is hydroxyl or amino group, these groups may be preferably protected by the protective groups, which is non-limiting and easily removed off by catalytic reduction, hydrolysis and enzyme reaction and the like (for example, "Protective Groups In Organic Synthesis" 2nd. ed., T. W. Green and P. G. M. Wuts, John Wiley & Sons, Inc., New York 1991). Examples of the protective group may include hydroxyl protecting group or amino protecting group such as benzyl, acetyl and the like commonly used in the field of organic chemistry, and benzyl group is preferably used. The compound of the formula (II) is commercial available or may be prepared from a commercial available compound by the common method in this technical field.

Furthermore, in catechins of the formula (II), the substitute represented by "$R^1$" may preferably be the hydroxyl protecting group, and the hydroxyl group of the sugar derivative represented by the formula (III) may preferably be protected by $R^3$, $R^4$ and $R^5$. The hydroxyl protecting group represented by $R^1$, $R^3$, $R^4$ and $R^5$ is non-limiting and easily removed by catalytic reduction, hydrolysis or enzyme reaction (for example, "Protective Groups In Organic Synthesis" 2nd. ed., T. W. Green and P. G. M. Wuts, John Wiley & Sons, Inc., New York 1991). Examples of the protective group include hydroxyl protecting group such as benzyl, acetyl and the like commonly used in the field of organic chemistry, and benzyl group is preferably used. The group $R^6$ of sugar derivative of the formula (III) may be hydrogen atom, hydroxyl group or hydroxyl group protected by $R^1$, $R^3$, $R^4$ and $R^5$ mentioned above. The compound of the formula (III) is commercial available or may be prepared from a commercial available compound by the common method in this technical field.

The process can be carried out in the suitable solvent by reacting 1.0 equivalent of the compound of the formula (II) with 0.5 to 2.0, preferably 1.0 equivalent of the compound of the formula (III) in the presence of $Cp_2HfCl_2$ or $Cp_2ZrCl_2$ together with AgX (in which, Cp is cyclopentadienyl group; X is $ClO_4$ or $CF_3SO_3$), or in the presence of Lewis acid.

The amount of $Cp_2HfCl_2$ or $Cp_2ZrCl_2$ as the reaction regent may be 0.5 to 2.0, preferably 1.0 to 1.5 equivalents based on 1.0 equivalent of the compound of the formula (III). Further, 2.0 equivalents of AgX (in which, X is $ClO_4$ or $CF_3SO_3$) based on the amount of the reaction reagent may be preferably used. Examples of AgX may include $AgClO_4$ or $CF_3SO_3Ag$.

In this reaction, Lewis acid may be used as the reaction reagent, and examples of the Lewis acid may include trimethysilyl triflate [TMS(OTf)], di-t-butylsilyl ditriflate [$t\text{-}Bu_2Si(OTf)_2$], boron trifluoride etherate [$BF_3OEt_2$], t-butyldimethylsilyl ditriflate [$t\text{-}BuMe_2Si(OTf)_2$], tin chloride and the like. The amount of the Lewis acid may be 0.5 to 3.0, preferably 0.5 to 2.0 equivalents based on the amount of the compound (II).

The solvent to be used in the reaction may be non-limiting inert solvent, for example halogenated hydrocarbons such as methylene chloride, ethylene chloride and the like; ethers such as diethyl ether, dioxane and the like; aromatic hydrocarbons such as toluene, benzene and the like. In the light of reaction selectivity, reaction yield, handling and so on, halogenated hydrocarbons such as methylene chloride or aromatic hydrocarbons such as toluene and benzene are preferably used.

The reaction time and reaction temperature are not strictly limited; however, the reaction temperature may range from $-78°$ C. to $100°$ C., particularly from $-78°$ C. to the room temperature. The reaction time may be decided by the index of the productivity of the purposed compound, and the compound of the formula (III) may be isolated and purified by subjecting the reaction mixture to ordinary means in the field of the organic chemistry such as condensation, extraction, solvent conversion, chromatography, and the like.

In this Process 1, the stereoisomer compound (optical isomer) due to the asymmetric carbon atoms of 2- and 3-positions of flavonoid skeleton can be used for catechins of the formula (II), and in this case, the compound (IV) having same configuration as the compound (II) can be obtained by the reaction with the compound of the formula (III).

Subsequently, the compound of the formula (IV) obtained by the Process 1 can be converted to the compound of the formula (V) by oxidation reaction using an oxidizing reagent in the suitable solvent, by the Process 2.

The oxidation reaction can be carried out by the following two methods (a) or (b).

(a) Method for obtaining the compound (V) by direct oxidation of the compound (IV), or (b) Method for obtaining the compound (V) by converting the compound (IV) to the intermediate compound of the formula (VI) by introducing hydroxyl group at 4-position of flavonoid skeleton, then, oxidation of the hydroxyl group at the 4-position of the compound (VI).

The oxidizing reagent used for the direct oxidation of the compound of the formula (IV) to obtain the compound of the formula (V) may be any type of the oxidizing reagent, which is used for oxidation of the 4-position of the flavonoid skeleton convert to oxo group, and lead tetraacetate, 2,3-dichloro-5,6-dicyanobenzoquinone (herein-after referred to as DDQ) or pyridinium dichromate (hereinafter referred to as PDC) is preferably used.

The solvent to be used in the oxidation reaction is not strictly limited and may be inert solvent, for example halogenated hydrocarbons such as methylene chloride, ethylene chloride and the like; ethers such as dioxane, tetrahydrofuran and the like; aromatic hydrocarbons such as benzene, toluene, and the like; water, or the mixture solvent thereof. The reaction temperature may range from $-78°$ C. to $100°$ C., preferably at the room temperature. The reaction time may be decided by the index of the productivity of the purpose compound, and the purpose compound of the formula (V) can be obtained in the good yield.

On the other hand, the oxidizing reagent used for the oxidation of the compound of the formula (IV) to obtain the intermediate compound of the formula (VI) by introducing hydroxyl group at 4-position of flavonoid skeleton, and then, oxidation of the hydroxyl group at the 4-position of the compound (VI) to obtain the compound of the formula (V) may be for example lead tetraacetate, 2,3-dichloro-5,6-dicyanobenzoquinone and the like. By using DDQ as the oxidizing reagent, hydroxyl group can be introduced at 4-position of flavonoid skeleton in good yield.

The oxidation reaction can be carried out in the suitable solvent, and examples of the solvent may include halogenated hydrocarbons such as methylene chloride, ethylene chloride and the like; ethers such as dioxane, tetrahydrofuran and the like; water, or the mixture solvent thereof, the mixture solvent of methylene chloride and water is preferably used. The reaction temperature may range from $-78°$ C. to $100°$ C., preferably at the room temperature. The reaction time may be decided by the index of the productivity of the purposed compound.

Then, the compound of the formula (VI) having hydroxyl group at 4-position of flavonoid skeleton is derived into the compound of the formula (V) by oxidation reaction of hydroxyl group to oxo group. The oxidizing reagent used for this reaction may be any type of the oxidizing reagent, which is used for oxidation of hydroxyl group, and pyridinium dichromate is preferably used.

The oxidation reaction of hydroxyl group can be carried out in the suitable solvent, and examples of the solvent may include halogenated hydrocarbons such as methylene chloride, ethylene chloride and the like; aromatic hydrocarbon such as benzene, toluene and the like; water, or the mixture solvent thereof. By using methylene chloride as the reaction solvent, the oxidation reaction can lead to a good result. The reaction temperature is not strictly limited and may range from $-78°$ C. to $100°$ C., preferably at the room temperature. The reaction time may be decided by the index of the productivity of the purposed compound.

Then, by the Process 3, the compound of the formula (V) obtained in the Process 2 is converted to astilbin and analogous thereof represented by the formula (I), which is the objective compound of the present invention, by removing the hydroxyl protecting group (de-protective reaction) of the compound (V).

The condition of the removing reaction of the hydroxyl protecting group in the Process 3 may vary depending on the variety of the hydroxyl protecting group. For example, in case of benzyl group is used as the protective group, the benzyl group can preferably removed by the hydrogenation reaction using of the catalyst. Examples of the catalyst may include Raney nickel, palladium-carbon (5 to 20%), palladium-black, platinum and the like, and the reaction can be carried out under hydrogen gas atmospheric pressure with stirring.

The reaction described above provides astilbin and analogues thereof represented by the formula (I) of the present invention, and the compound of the formula (I) may be obtained in purity form after the reaction by the ordinary means in the field of the organic chemistry such as condensation, extraction, solvent conversion, chromatography, and the like.

EXAMPLE

The present invention is described in more detail in the following by way of working examples; however, it is to be understood that the present invention is not limited to the examples.

In the description of the example, number in parenthesis is the number of the compound, and the symbols listed below are used to have the particular meanings respectively.

| | |
|---|---|
| Ac | acetyl group |
| Bn | benzyl group |
| OTf | $CF_3SO_3$ |
| Cp | cyclopentadienyl group |

Example 1

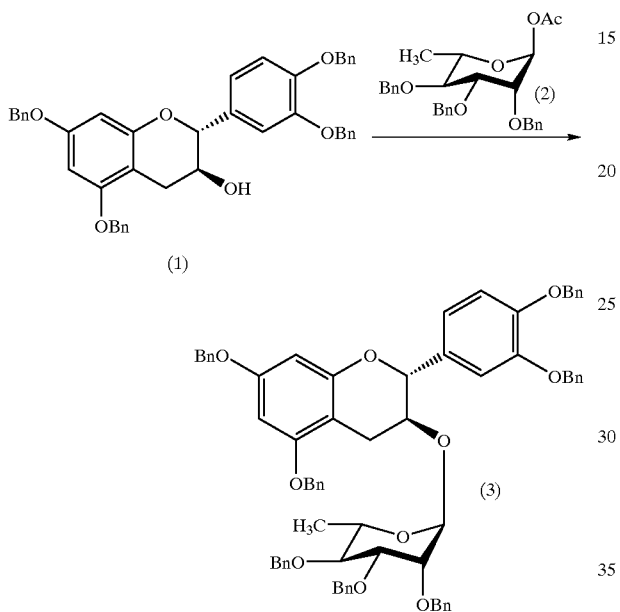

To a mixture solution of 83.0 mg (0.218 mmol) of $Cp_2HfCl_2$ and 90.8 mg (0.439 mmol) of $AgClO_4$ in methylene chloride in the presence of 214 mg of pulverized and dried desiccant (molecular sieve 4A) were sequential added a solution of 127 mg (0.195 mmol) of Compound (1) in methylene chloride (3.0 ml) and a solution of 93.7 mg (0.197 mmol) of Compound (2) in methylene chloride (3.0 ml) at −78° C. Then, the temperature of the reaction mixture was gradually increased up to −35° C. during 1 hour, and the reaction mixture was stirred for 1 hour at the same temperature. After the reaction, saturated sodium hydrogen carbonate aqueous solution (2.0 ml) was added dropwise to the reaction mixture, and insoluble materials were removed off by Celite® filtration. Water was added to the obtained filtrate, and the mixture was extracted with ethyl acetate (thrice). The combined organic layer was washed with brine and dried over with anhydrous sodium sulfate. The solvent was removed under reduced pressure, and the resultant crude product was purified by preparative silica gel chromatography (benzene/ethyl acetate=98/2) to obtain 70.1 mg (yield: 82%) of Compound (3) as white solid.

Data of the instrumental analysis of the Compound (3) were as follow:

Melting point: 36–38° C.

$[\alpha]_D^{22}$: +26.2 (c=1.05, $CHCl_3$)

$^1$H-NMR (500 MHz, $CDCl_3$) δ 1.27 (d, 3H, J=6.3 Hz), 2.66 (dd, 1H, J=16.5, 9.0 Hz), 3.06 (dd, 1H, J=16.5, 6.0 Hz), 3.36 (dd, 1H, $J_1$=3.0, $J_2$=1.5 Hz), 3.52 (dd, 1H, $J_1$=9.5, $J_2$=9.5 Hz), 3.75 (dd, 1H, $J_1$=9.5, $J_2$=3.0 Hz), 3.79 (dq, 1H, $J_1$=9.5, $J_2$=6.3 Hz), 3.96 (ddd, 1H, $J_1$=9.0, $J_2$=9.0, $J_3$=6.0 Hz), 4.20 (d, 1H, J=12.5 Hz), 4.259 (d, 1H, J=1.5 Hz), 4.263 (d, 1H, J=12.5 Hz), 4.48 (d, 1H, J=11.5 Hz), 4.54 (d, 1H, J=11.5 Hz), 4.59 (d, 1H, J=10.8 Hz), 4.60 (d, 1H, J=9.0 Hz), 4.89 (d, 1H, J=10.8 Hz), 4.98 (s, 2H), 5.03 (d, 1H, J=12.0 Hz), 5.05 (d, 1H, J=12.0 Hz), 5.09 (s, 2H), 5.12 (s, 2H), 6.18 (d, 1H, J=2.5 Hz), 6.24 (d, 1H, J=2.5 Hz), 6.90 (dd, 1H, $J_1$=8.0, $J_2$=1.5 Hz), 6.90 (dd, 1H, J=8.0 Hz), 7.06 (d, 1H, J=1.5 Hz), 7.19–7.21 (m, 5H), 7.25–7.43 (m, 30H).

$^{13}$C-NMR (125 MHz, $CDCl_3$) δ 17.9, 27.9, 68.5, 70.0, 70.1, 71.3, 71.4, 71.9, 72.4, 74.2, 75.4, 75.5, 79.7, 80.1, 80.4, 93.9, 94.4, 98.1, 102.5, 114.0, 114.7, 120.8, 127.12, 127.14, 127.39, 127.41, 127.50, 127.54, 127.7, 127.80, 127.84, 127.9, 128.0, 128.1, 128.2, 128.3, 128.4, 128.475, 128.483, 128.5, 128.6, 131.9, 136.9, 136.96, 137.00, 137.1, 138.2, 138.5, 138.7, 149.1, 149.2, 155.3, 157.6, 158.8.

IR (KBr): $cm^{-1}$ 3030, 2910, 2865, 1950, 1875, 1810, 1750, 1620, 1590, 1515, 1500, 1455, 1430, 1375, 1310, 1260, 1215, 1145, 1120, 1095, 910, 840, 810, 735, 695, 615.

Elemental analysis for $C_{70}H_{66}O_{10}$ Calcd.: C, 78.78; H, 6.23. Found: C, 77.82; H, 6.23.

Example 2

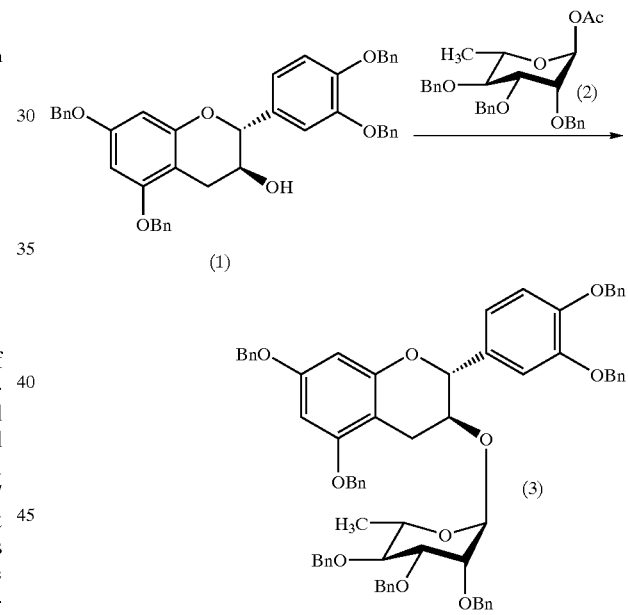

A mixture solution of 87.4 mg (0.134 mmol) of Compound (1) and 64.3 mg (0.135 mmol) of Compound (2) in methylene chloride (4.0 ml) in the presence of 204 mg of pulverized and dried desiccant (molecular sieve 4A) was cooled to −78° C. To this mixture was added a solution of t-$Bu_2Si(OTf)_2$ in methylne chloride (0.48 ml: 0.15 mmol), then, the temperature of the reaction mixture was gradually increased up to −20° C. during 3 hours, and the reaction mixture was stirred for 50 minutes at the same temperature. After the reaction, aqueous saturated sodium hydrogen carbonate solution (2.0 ml) was added dropwise to the reaction mixture, and insoluble materials were removed off by Celite® filtration. Water was added to the obtained filtrate, and the mixture was extracted with ethyl acetate (thrice). The combined organic layer was washed with brine and dried over anhydrous sodium sulfate. The solvent was removed off under reduced pressure, and the resultant crude product was purified by preparative silica gel chromatography (benzene/ethyl acetate=97/3) to obtain 109 mg (yield: 76%) of Compound (3) as colorless solid and 12.5 mg (yield: 9%) of stereoisomer of Compound (3) as colorless solid, as by product.

Data of the instrumental analysis of the Compound (3) were identified with those obtained in Example 1.

Example 3

The Compound (3) was obtained by repeating the same reaction described in the Example 2, by replacing the reaction solvent and the reaction reagent as indicated in the following table.

The yields were summarized in the following table.

| Reaction Reagent | Reaction Temperature | Reaction Solvent | Yield (%) of the Compound (3) |
|---|---|---|---|
| $Cp_2ZrCl_2$—$AgClO_4$ | −78° C.~−35° C. | $CH_2Cl_2$ | 74 |
| $Cp_2ZrCl_2$—$Ag(OTf)$ | −78° C.~room tempt. | $CH_2Cl_2$ | 3 |
| $BF_3OEt_2$ | −78° C.~room tempt. | $CH_2Cl_2$ | 38 |
| $SnCl_4$ | −78° C.~−28° C. | $CH_2Cl_2$ | 10 |
| TMS(OTf) | −78° C.~−30° C. | $CH_2Cl_2$ | 55 |
| $Ph_2SiCl_2$—$AgClO_4$ | −78° C.~−40° C. | $CH_2Cl_2$ | 43 |
| $t$-$Bu_2Si(OTf)_2$ | −78° C.~room tempt. | $CH_2Cl_2$ | 66 |
| $i$-$Pr_3Si(OTf)$ | −78° C.~room tempt. | $CH_2Cl_2$ | 63 |
| $t$-$Bu_2Si(OTf)_2$ | −78° C.~−10° C. | $CH_2Cl_2$ | 52 |
| $t$-$Bu_2Si(OTf)_2$ | −78° C.~room tempt. | Ether | 61 |
| $t$-$Bu_2Si(OTf)_2$ | −78° C.~room tempt. | Benzene | 70 |
| $t$-$Bu_2Si(OTf)_2$ | 0° C. | Toluene | 68 |

Example 4

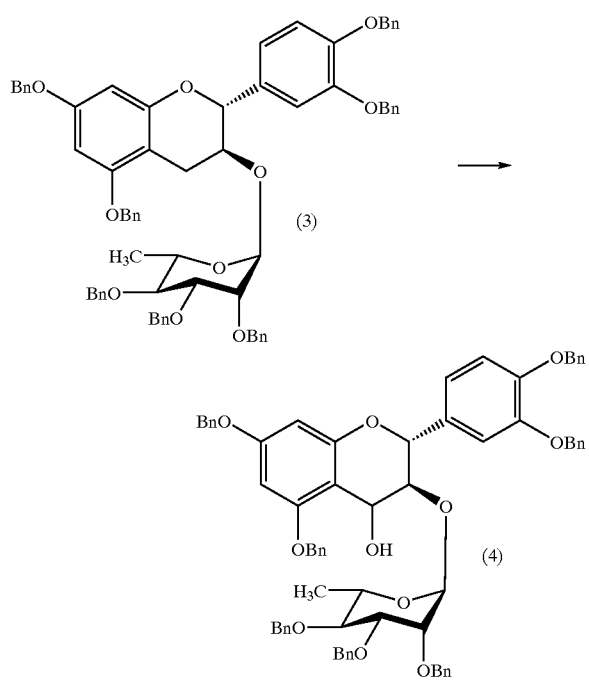

To a solution of 28.5 mg (0.0267 mmol) of Compound (3) in methylene chloride (2.7 ml) were sequential added 12.6 mg (0.0555 mmol) of 2,3-dichloro-5,6-dicyanobenzoquinone (DDQ) and water (0.14 ml; 7.8 mmol), and the mixture was stirred for 5 hours at the room temperature. The reaction mixture was cooled to 0° C., then water and ether were added to the mixture. The mixture was extracted with ether (thrice) and the combined organic layer was washed with saturated aqueous sodium hydrogen carbonate solution (twice) and brine (thrice), and dried over with anhydrous sodium sulfate. The solvent was removed off under reduced pressure, and the resultant crude product was purified by preparative silica gel chromatography (benzene/ethyl acetate=95/5) to obtain 19.1 mg (yield: 66%) of Compound (4) as colorless solid.

Data of the instrumental analysis of the Compound (4) were as follow:

Melting point: 40–42° C.

$[\alpha]_D^{23}$: +36.7 (C=1.04, $CHCl_3$)

$^1$H-NMR (500 MHz, $CDCl_3$) δ 1.28 (d, 3H, J=6.0 Hz), 2.46 (brs, 1H, OH), 3.36 (dd, 1H, $J_1$=3.0, $J_2$=1.5 Hz), 3.51 (dd, 1H, $J_1$=$J_2$=9.5 Hz), 3.73 (dd, 1H, $J_1$=9.5, $J_2$=3.0 Hz), 3.83 (dq, 1H, $J_1$=9.5, $J_2$=6.0 Hz), 3.95 (dd, 1H, $J_1$=10.0, $J_2$=3.0 Hz), 4.09 (d, 1H, J=12.5 Hz), 4.18 (d, 1H, J=12.5 Hz), 4.20 (d, 1H, J=1.5 Hz), 4.45 (d, 1H, J=12.0 Hz), 4.53 (d, 1H, J=12.0 Hz), 4.58 (d, 1H, J=11.0 Hz), 4.88 (d, 1H, J=11.0 Hz), 4.97 (d, 1H, J=13.0 Hz), 4.99 (d, 1H, J=13.0 Hz), 5.06–5.11 (m, 5H), 5.12–5.15 (m, 3H), 6.15 (d, 1H, J=2.0 Hz), 6.25 (d, 1H, J=2.0 Hz), 6.95 (d, 1H, J=8.0 Hz), 7.01 (dd, 1H, $J_1$=8.0, $J_2$=2.0 Hz), 7.14 (d, 1H, J=2.0 Hz), 7.16–7.42 (m, 35H).

$^{13}$C-NMR (125 MHz, $CDCl_3$) δ 17.9, 61.9, 69.0, 70.1, 70.3, 71.2, 71.4, 72.0, 72.4, 74.7, 75.31, 75.34, 77.1, 79.5, 80.1, 94.3, 94.4, 98.5, 104.7, 114.5, 114.6, 121.1, 127.1, 127.37, 127.41, 127.45, 127.48, 127.5, 127.6, 127.7, 127.8, 127.88, 127.93, 128.0, 128.1, 128.2, 128.3, 128.4, 128.47, 128.49, 128.59, 128.61, 131.3, 136.6, 136.7, 136.9, 137.0, 138.0, 138.4, 138.5, 149.1, 149.4, 155.9, 158.6, 160.9.

IR (KBr): $cm^{-1}$ 3435, 3030, 2915, 1615, 1595, 1515, 1495, 1455, 1430, 1375, 1265, 1210, 1150, 1120, 1050, 1030, 905, 810, 735, 695, 624.

Example 5

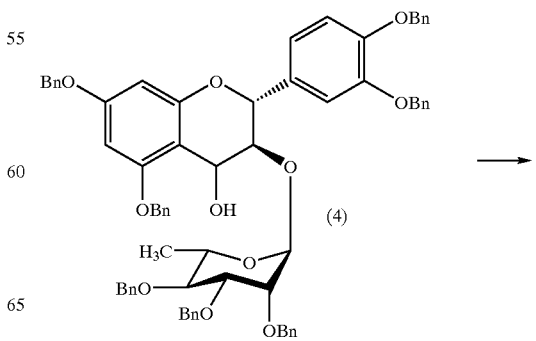

-continued

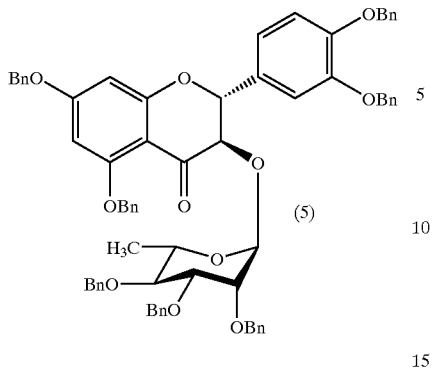

To a solution of 35.7 mg (0.0330 mmol) of Compound (4) in methylene chloride (3.0 ml) was added pyridinium dichromate (24.9 mg; 0.0662 mmol) at 0° C., and the mixture was stirred for 21 hours at the room temperature. Then, pyridinium dichromate (26.9 mg; 0.0715 mmol) was further added to the reaction mixture at 0° C., and the mixture was stirred for 19 hours at the room temperature. After the reaction mixture was cooled to 0° C., the reaction was stopped by adding ether. The mixture was filtrated by Celite® and the solvent was removed off under reduced pressure. The resultant crude product was purified by preparative silica gel chromatography (benzene/ethyl acetate= 95/5) to obtain 30.2 mg (yield: 85%) of Compound (5) as colorless solid.

Data of the instrumental analysis of the Compound (5) were as follow:

Melting point: 47–49° C.

$[\alpha]_D^{24}$: +25.7 (C=1.03, CHCl$_3$)

$^1$H-NMR (500 MHz, CDCl$_3$) δ 1.22 (d, 3H, J=6.0 Hz), 3.47 (dd, 1H, J$_1$=3.3, J$_2$=1.5 Hz), 3.52 (dd, 1H, J$_1$=J$_2$=9.5 Hz), 3.91 (dd, 1H, J$_1$=9.5, J$_2$=3.3 Hz), 4.179 (d, 1H, J=1.5 Hz), 4.180 (d, 1H, J=12.5 Hz), 4.23 (d, 1H, J=12.5 Hz), 4.33 (dq, 1H, J$_1$=9.5, J$_2$=6.0 Hz), 4.44 (d, 1H, J=11.0 Hz), 4.49 (d, 1H, J=11.5 Hz), 4.61 (d, 2H, J=11.5 Hz), 4.90 (d, 1H, J=11.5 Hz), 5.01 (s, 2H), 5.08 (s, 2H), 5.12 (d, 1H, J=11.0 Hz), 5.13 (s, 2H), 5.19 (s, 2H1), 6.16 (d, 1H, J=2.2 Hz), 6.21 (d, 1H, J=2.2 Hz), 6.94 (d, 1H, J=8.0 Hz), 6.98 (dd, 1H, J$_1$=8.0, J$_2$=2.0 Hz), 7.12 (d, 1H, J=2.0 Hz), 7.18–7.43 (m, 33H), 7.52 (d, 2H, J=7.5 Hz).

$^{13}$C-NMR (125 MHz, CDCl$_3$) δ 17.9, 68.8, 70.3, 70.5, 71.2, 71.4, 72.2, 72.4, 74.9, 76.0, 78.2, 79.7, 80.4, 82.3, 94.7, 95.6, 98.0, 105.5, 114.0, 114.5, 126.5, 127.1, 127.3, 127.29, 127.33, 127.38, 127.39, 127.50, 127.52, 127.6, 127.8, 127.86, 127.93, 128.1, 128.2, 128.4, 128.50, 128.52, 128.6, 128.7, 129.6, 135.7, 136.4, 136.8, 136.9, 138.3, 138.9, 139.0, 149.2, 149.8, 161.2, 163.9, 164.8, 186.7.

IR (KBr): cm$^{-1}$ 3030, 2930, 1955, 1695, 1610, 1575, 1515, 1455, 1430, 1380, 1265, 1235, 1215, 1165, 1115, 1030, 820, 750, 695, 670.

Elemental analysis for C$_{70}$H$_{64}$O$_{11}$ Calcd.: C, 77.76; H, 5.97. Found: C, 77.54; H, 6.27.

Example 6

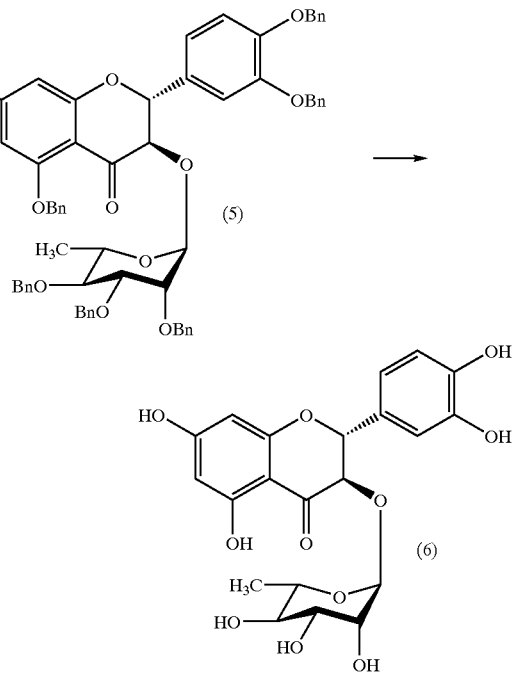

To a solution of 39.5 mg (0.0365 mmol) of Compound (5) in methanol (5.0 ml) was added palladium black (3.0 mg), and the mixture was stirred for 20 hours under hydrogen atmosphere at the room temperature. Then, palladium black (3.0 mg) was further added to the reaction mixture and the mixture was stirred for 30 hours under hydrogen atmosphere. After the reaction mixture was leaved for rest, the supernatant liquid was collected, and the residue stirred with methanol. After the mixture was leaved for rest, the supernatant liquid was collected. This procedure was repeated thrice. All collected was combined and removed off under reduced pressure. The resultant residue was purified by Sephadex® LH-20 to obtain 14.9 mg (yield: 91%) of Compound (6) [astilbin] as colorless solid.

Data of the instrumental analysis of the Compound (6) were as follow:

$^1$H-NMR (500 MHz, CDCl$_3$) δ 1.18 (d, 3H, J=6.0 Hz), 3.30 (dd, 1H, J$_1$=J$_2$=9.5 Hz, overlapping with MeOH), 3.54 (dd, 1H, J$_1$=3.3, J$_2$=1.3 Hz), 3.65 (dd, 1H, J$_1$=9.5, J$_2$=3.3 Hz), 4.05(d, 1H, J=1.3 Hz), 4.23 (dq, 1H, J$_1$=9.5, J$_2$=6.0 Hz), 4.56 (d, 1H, J=10.5 Hz), 5.06 (d, 1H, J=10.5 Hz), 5.89(d, 1H, J=2.0 Hz), 5.91 (d, 1H, J=2.0 Hz), 6.80 (d, 1H, J=8.3 Hz), 6.83 (dd, 1H, J$_1$=8.3, J$_2$=1.8 Hz), 6.95 (d, 1H, J=1.8 Hz).

$^{13}$C-NMR (125 MHz, CD$_3$OD) δ 18.6, 71.3, 72.6, 73.0, 74.6, 79.4, 84.7, 97.1, 98.2.

INDUSTRIAL APPLICABILITY

As described above, the present invention is to provide a process for preparing a flavonoid compound having aldose reductase inhibitory effect, active oxygen extinguishing effect, carcinogenesis promotion inhibitory effect, anti-inflammatory effect, and so on, more particularly, to provide the industrial process for preparing astilbin and analogous thereof from the easily obtainable starting compound with short process and convenient means in high yield and high purity of the compound, and therefore, the present invention makes a great contribution to the medical and pharmaceutical industry.

What is claimed is:

1. A process for preparing a compound represented by the following formula (I):

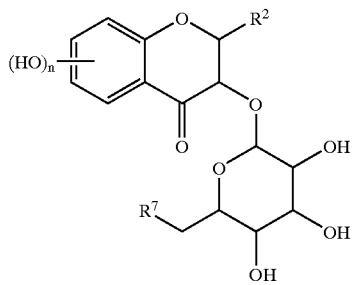

wherein, $R^2$ is a substituted or un-substituted phenyl group; $R^7$ is a hydrogen atom or a hydroxyl group; and n is an integer of 1 to 4;

which process is characterized in that reacting a compound of the following formula (II):

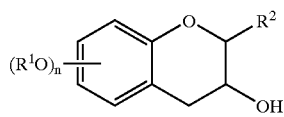

wherein, $R^1$ is a hydroxyl protecting group; $R^2$ and n have the same meanings mentioned above, with a sugar compound of the following formula (III):

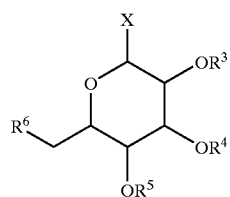

wherein, $R^3$, $R^4$ and $R^5$ are independently each other, a hydrogen atom or a hydroxyl protecting group; $R^6$ is a hydrogen atom, a hydroxyl group or a protected hydroxyl group; and X is a halogen atom or an acyloxy group, to produce a compound of following formula (IV):

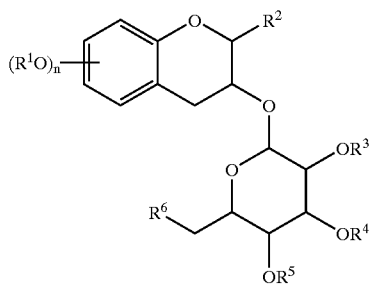

wherein, $R^1$, $R^2$, $R^3$, $R^4$, $R^5$, $R^6$ and n have the same meanings mentioned above, then, oxidizing of 4-position of the flavonoid skeleton of the compound of the formula (IV) obtained above to produce a compound of the following

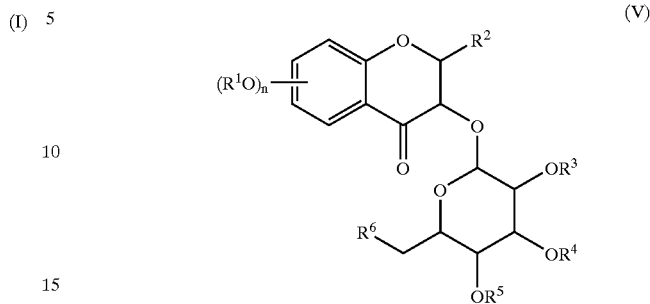

wherein, $R^1$, $R^2$, $R^3$, $R^4$, $R^5$, $R^6$ and n have the same meanings mentioned above, and removing the hydroxyl protecting group of the compound of the formula (V) obtained above to produce the compound of the formula (I).

2. A process for preparing a compound represented by the following formula (I):

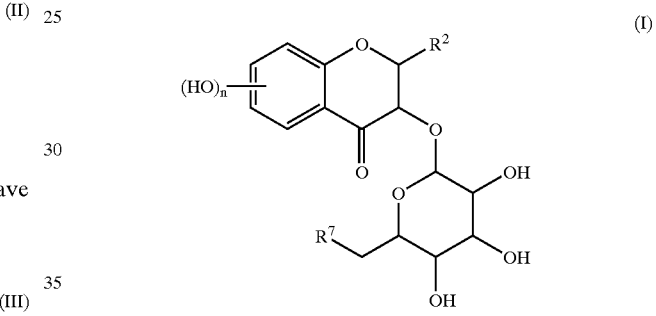

wherein, $R^2$ is a substituted or un-substituted phenyl group; $R^7$ is a hydrogen atom or a hydroxyl group; and n is an integer of 1 to 4;

which process is characterized in that reacting a compound of the following formula (II):

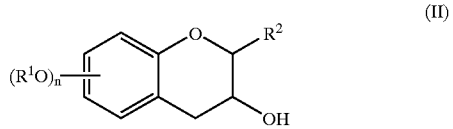

wherein, $R^1$ is a hydroxyl protecting group; $R^2$ and n have the same meanings mentioned above, with a sugar compound of the following formula (III):

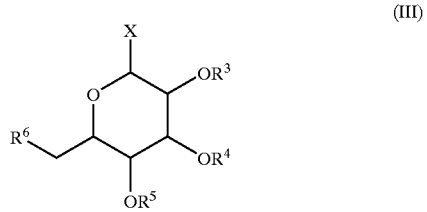

wherein, $R^3$, $R^4$ and $R^5$ are independently each other, a hydrogen atom or a hydroxyl protecting group; $R^6$ is a hydrogen atom, a hydroxyl group or a protected hydroxyl group; and X is a halogen atom or an acyloxy group, to produce a compound of following formula (IV):

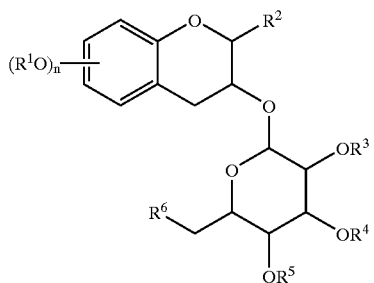

(IV)

wherein, $R^1$, $R^2$, $R^3$, $R^4$, $R^5$, $R^6$ and n have the same meanings mentioned above, then, oxidizing of 4-position of the flavonoid skeleton of the compound of the formula (IV) obtained above to produce a compound of the following formula (VI):

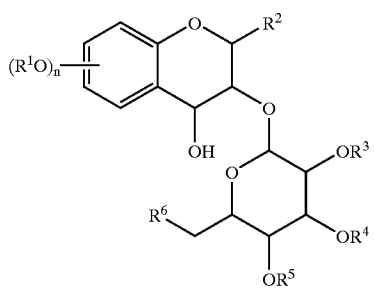

(VI)

wherein, $R^1$, $R^2$, $R^3$, $R^4$, $R^5$, $R^6$ and n have the same meanings mentioned above, subsequently, further oxidizing of 4-position of the flavonoid skeleton of the compound of the formula (VI) obtained above to produce a compound of the following formula (V):

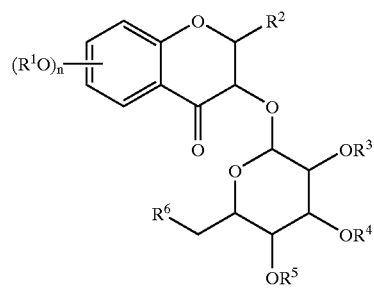

(V)

wherein, $R^1$, $R^2$, $R^3$, $R^4$, $R^5$, $R^6$ and n have the same meanings mentioned above, and removing the hydroxyl protecting group of the compound of the formula (V) obtained above to produce the compound of the formula (I).

3. A process for preparing a compound represented by the following formula (I):

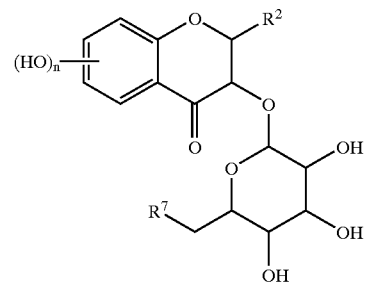

(I)

wherein, $R^2$ is a substituted or un-substituted phenyl group; $R^7$ is a hydrogen atom or a hydroxyl group; and n is an integer of 1 to 4;

which process is characterized in that oxidizing of 4-position of the flavonoid skeleton of a compound of the following formula (IV):

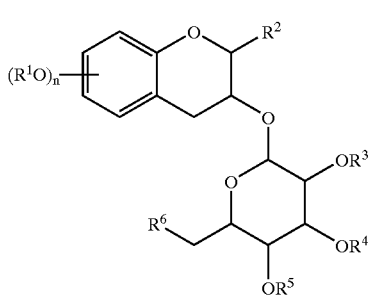

(IV)

wherein, $R^1$ is a hydroxyl protecting group; $R^2$ is a substituted or un-substituted phenyl group; $R^3$, $R^4$ and $R^5$ are independently each other, a hydrogen atom or a hydroxyl protecting group; $R^6$ is a hydrogen atom, a hydroxyl group or a protected hydroxyl group; and n is an integer of 1 to 4, to produce a compound of the following formula (V):

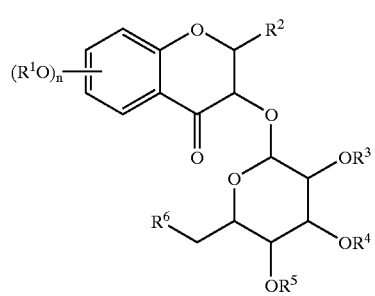

(V)

wherein, $R^1$, $R^2$, $R^3$, $R^4$, $R^5$, $R^6$ and n have the same meanings mentioned above, and removing the hydroxyl protecting group of the compound of the formula (V) obtained above to produce the compound of the formula (I).

4. A process for preparing a compound represented by the following formula (I):

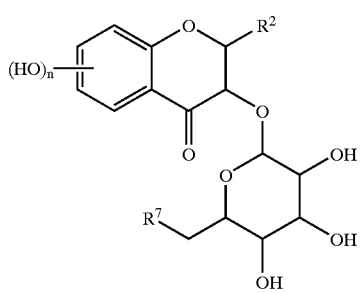

(I)

wherein, $R^2$ is a substituted or un-substituted phenyl group; $R^7$ is a hydrogen atom or a hydroxyl group; and n is an integer of 1 to 4;

which process is characterized in that oxidizing of 4-position of the flavonoid skeleton of a compound of the following formula (IV):

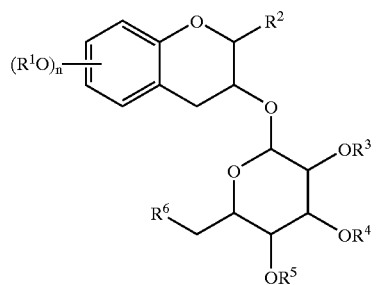

(IV)

wherein, $R^1$ is a hydroxyl protecting group; $R^2$ is a substituted or un-substituted phenyl group; $R^3$, $R^4$ and $R^5$ are independently each other, a hydrogen atom, a hydroxyl group or a hydroxyl protecting group; $R^6$ is a hydrogen atom, a hydroxyl group or a protected hydroxyl group; and n is an integer of 1 to 4;

to produce a compound of the following formula (VI):

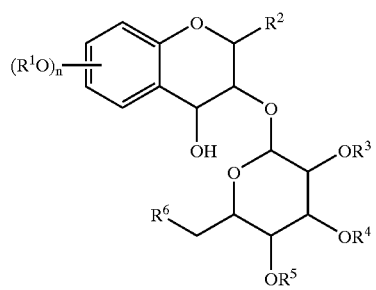

(VI)

wherein, $R^1$, $R^2$, $R^3$, $R^4$, $R^5$, $R^6$ and n have the same meanings mentioned above, subsequently, further oxidizing of 4-position of the flavonoid skeleton of the compound of the formula (VI) obtained above to produce a compound of the following formula (V):

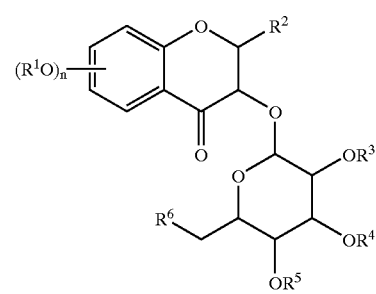

(V)

wherein, $R^1$, $R^2$, $R^3$, $R^4$, $R^5$, $R^6$ and n have the same meanings mentioned above, and removing the hydroxyl protecting group of the compound of the formula (V) obtained above to produce the compound of the formula (I).

5. The process according to any one of claims 1 to 4, wherein the compound of the formula (I) is a compound of the following formula (I-a):

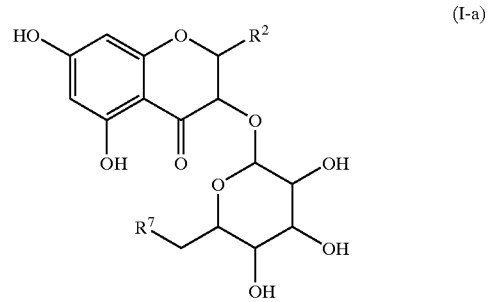

(I-a)

wherein, $R^2$ is a substituted or un-substituted phenyl group; $R^7$ is a hydrogen atom or a hydroxyl group.

6. The process according to any one of claims 1 to 4, wherein the compound of the formula (I) is a compound of the following formula (I-b):

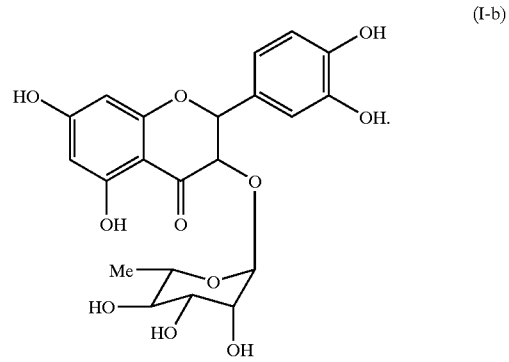

(I-b)

7. The process according to any one of claims 1 to 4, wherein the compound of the formula (I) is a compound of the following formula (I-c):

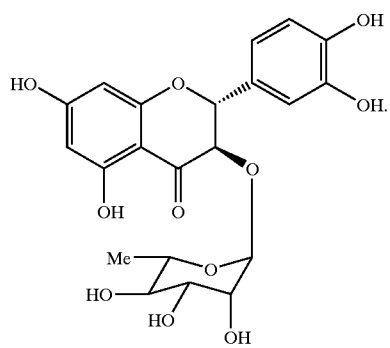

(I-c)

8. A process for preparing a compound represented by the following formula (V):

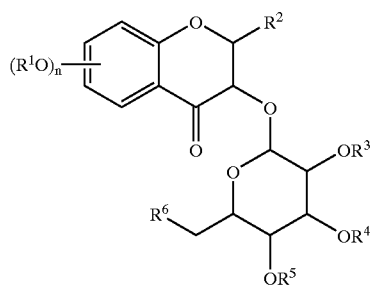

(V)

wherein, $R^1$ is a hydroxyl protecting group; $R^2$ is a substituted or un-substituted phenyl group; $R^3$, $R^4$ and $R^5$ are independently each other, a hydrogen atom or a hydroxyl protecting group; $R^6$ is a hydrogen atom, a hydroxyl group or a protected hydroxyl group; and n is an integer of 1 to 4, which process is characterized in that oxidizing of 4-position of the flavonoid skeleton of a compound of the following formula (IV):

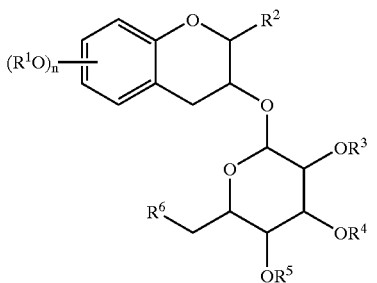

(IV)

wherein, $R^1$, $R^2$, $R^3$, $R^4$, $R^5$, $R^6$ and n have the same meanings mentioned above.

9. A process for preparing a compound represented by the following formula (V):

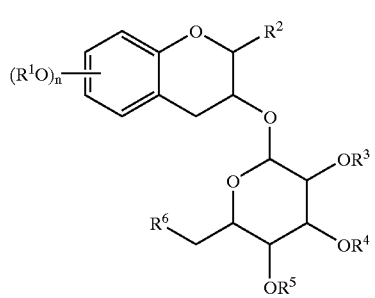

(V)

wherein, $R^1$ is a hydroxyl protecting group; $R^2$ is a substituted or un-substituted phenyl group; $R^3$, $R^4$ and $R^5$ are independently each other, a hydrogen atom or a hydroxyl protecting group; $R^6$ is a hydrogen atom, a hydroxyl group or a protected hydroxyl group; and n is an integer of 1 to 4, which process is characterized in that oxidizing of 4-position of the flavonoid skeleton of a compound of the following formula (IV):

(IV)

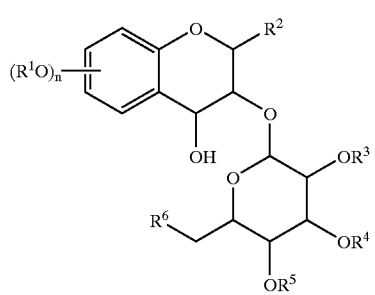

wherein, $R^1$, $R^2$, $R^3$, $R^4$, $R^5$, $R^6$ and n have the same meanings mentioned above, to produce a compound of the following formula (VI):

(VI)

wherein, $R^1$, $R^2$, $R^3$, $R^4$, $R^5$, $R^6$ and n have the same meanings mentioned above, and further oxidizing of 4-position of the flavonoid skeleton of the compound of the formula (VI) obtained above to produce a compound of the following formula (V).

* * * * *